July 8, 1958 R. S. MOORE Plant Pat. 1,726

MINIATURE ROSE PLANT

Filed Aug. 27, 1957

WITNESS

Addison E. Avery

INVENTOR

Ralph S. Moore

Webster & Webster

ATTYS.

United States Patent Office

Plant Pat. 1,726

Patented July 8, 1958

1,726

MINIATURE ROSE PLANT

Ralph S. Moore, Visalia, Calif.

Application August 27, 1957, Serial No. 680,605

1 Claim. (Cl. 47—61)

This invention is directed to a new and distinct hybrid, miniature bush rose plant which bears—in general appearance—relatively dark, ruby red flowers.

The variety was originated by me in my nursery at Visalia, California as a cross between an unnamed seedling (Rosa Wichuriana × Floradora) as the seed parent, and another unnamed seedling (Oakington Ruby × Floradora) as the pollen parent.

When such cross grew to maturity, and its desirable features noted by me in the course of careful and continuing observations, I asexually reproduced the variety by cuttings, and these have—in full growth—reflected all of the botanical characteristics of the parent seedling.

Such reproduction of the variety was accomplished by me in my nursery located as aforesaid.

In general, the plant of the present variety of miniature rose is well shaped, dense, and fills out substantially to the soil level; the foliage being clean, a medium to dark green, and glossy, whereby the plant is ornamental whether or not with flowers. The cuttings root readily and transplant easily, while the plant withstands shearing very well, with the bloom recurring or repeating rather quickly.

In comparison to other miniature roses the instant variety is—on the average—more vigorous in growth; the plant having—for example—greater vigor, more thorns, and deeper red flowers than the aforementioned Oakington Ruby.

Further, the greater vigor of growth, together with being more upright and having deeper and more lasting red flowers, is evident in comparison to the Juliette.

Additionally, the present variety of miniature rose is larger in plant size, and a heavier plant with darker, larger, and less double red flowers than the Red Imp (United States Plant Patent No. 1,032).

Figure 3:
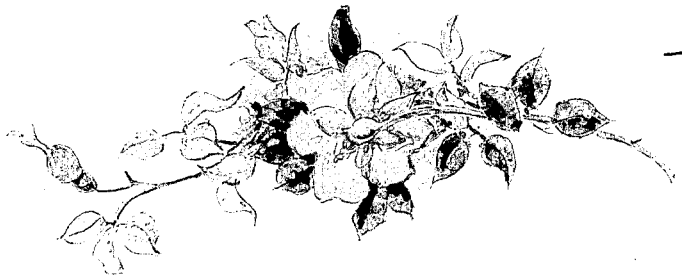
Fig. 3 is a similar view, but the rear of the flower is shown.
Figure 1:
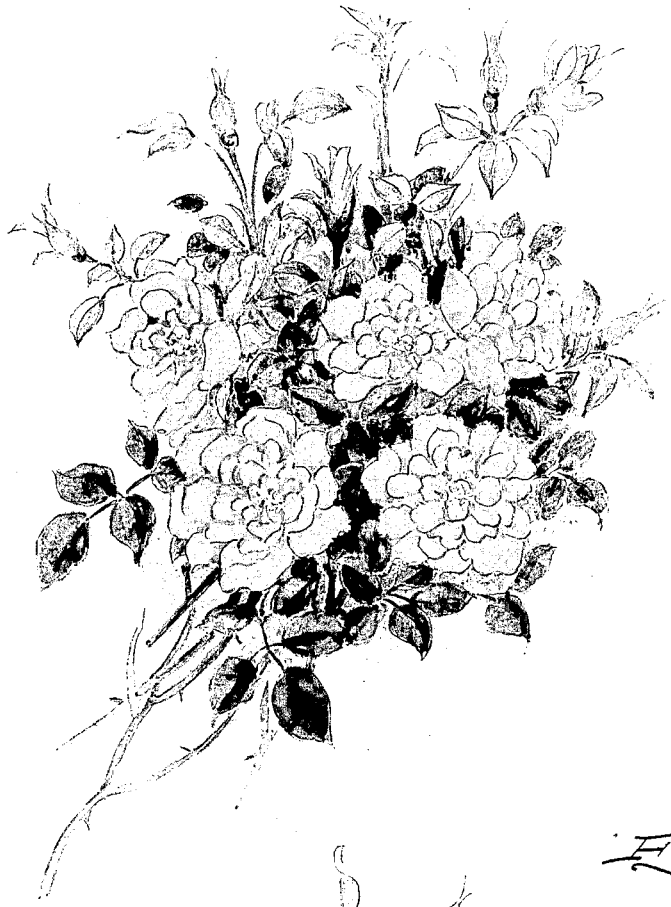
Fig. 1 shows a spray, including foliage, buds, and flowers.
Figure 2:
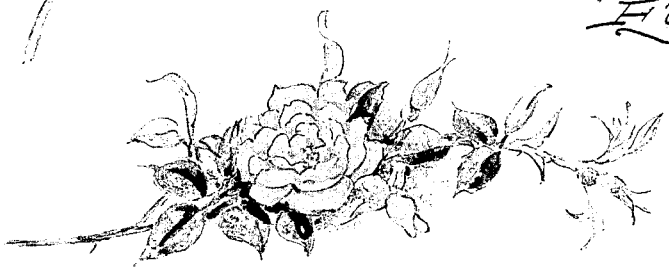
Fig. 2 is an elevation of a single stem, with a flower and buds; the front of the flower being shown.

Referring now specifically to the new and distinct variety of miniature rose plant, the following is a detailed description thereof in outline; all major color plate identifications being by Maerz and Paul Dictionary of Color, except where otherwise indicated, or where common terms of color definition are employed.

Type: Bush; dwarf; hardy; outdoors; cut flowers; garden decoration.

Class: Hybrid miniature.

*Flower*

Continuity: Continuous.

Fragrance: Slight.

Flowers borne: Singly—several borne in an irregular cluster on a strong short stem.

Quantity of bloom: Free, outdoors.

Bud:

*Peduncle.*—Medium length; heavy; erect; stiff; medium green; few brown hairs.

*Before calyx breaks.*—Size—small. Form—pointed, with foliaceous appendages and with much cut foliaceous parts extending beyond tip of the bud equal to one-half or more of its length. Color—medium green—sometimes slightly reddish.

*As calyx breaks.*—Color—deep red.

*As first petal opens.*—Size—small. Form—pointed; ovoid. Color—deep red.

Bloom:

*Size when fully open.*—Average 1¼" to 1½".

*Petalage.*—Double, with from 15 to 25 petals (sometimes 35 to 40 petals) arranged irregularly.

*Form.*—Cupped, becoming flat and open petals flat cupped, with some outer petals rolled outwardly.

Petals: Thick; leathery; velvety; shiny.

*Shape.*—Outside—ovate, with acuminate tip. Intermediate—oblanceolate. Inside—lanceolate.

*Color (by reference to British Colour Council Horticultural Chart).*—Generally a deep or ruby red (827/1 to 827/3). While the general appearance is deep red, the petals—on a newly opened flower—shade from white at the immediate base to tyrian rose (24–3) and then to such deep red, which subsequently becomes the entire color of the petal.

*Behavior.*—Drops off cleanly.

*Flower longevity.*—3 to 5 days.

Reproductive organs:

*Stamens.*—Few to medium in number; irregularly arranged; sometimes mixed with petaloids.

*Filaments.*—Short; most with anthers; white.

*Anthers.*—Small; open at once; yellow.

*Pollen.*—Sparse; lemon.

*Pistils.*—Few.

*Styles.*—Short; medium; bunched.

*Stigma.*—White.

*Ovaries.*—All enclosed in calyx.

*Hips.*—None.

*Sepals.*—Permanent; long. Spear shaped—rather prominent like green stars. Recurved; green.

*Seeds.*—None.

*Plant*

Foliage:

*Leaves.*—Compound of three to five leaflets; abundant; small; heavy; leathery; glossy.

*Leaflets.*—Oval—ovoid. Apex acute; base round; margin serrate.

*Color of leaves.*—Mature leaves: top side—medium to dark green (22–L–9); under side—somewhat lighter green (21–K–7). Young leaves: greenish bronze (12–L–7, shading to 15–A–12).

*Rachis.*—Heavy. Upper side—grooved, hairy. Under side—moderately hairy, with an average of two small thorns.

*Stipules.*—Medium length. Narrow, with medium length points, turning out at an angle of about 45 degrees. In fully mature leaves the angle is somewhat less.

Growth:

*Habit.*—Dwarf; bushy; much branched.

*Growth.*—Vigorous.

*Canes.*—Medium. Average—16" tall.

*Main stems.*—Color—green. Thorns—several; medium length; slightly hooked downward; reddish brown to brown when immature and grey (5–A–11) when mature. Prickles—none to few. Hairs—none.

*Branches.*—Color—green; slightly lighter in color than leaves. Prickles—none. Hairs—none.

*New shoots.*—Color—green. Thorns—several; medium length; hooked downward; base oval. Prickles—none to few. Hairs—none to few.

With the exception of the Red Imp (United States Plant Patent No. 1,032), all of the other mentioned existing varieties are unpatented.

The miniature rose plant and its flowers as herein described may vary in slight detail due to climatic and soil conditions under which the variety may be grown.

The following is claimed:

A new and distinct variety of bush type hybrid miniature rose plant, substantially as described and illustrated, characterized by a dense, well-shaped plant having foliage which fills out approximately to soil level, and which foliage is clean, medium to dark green, and glossy; further characterized by cuttings which root readily and transplant easily, and a plant which withstands shearing very well, with the bloom recurring quickly; and additionally characterized in comparison with the Oakington Ruby by greater vigor of growth, more thorns, and deeper red flowers; in comparison with the Juliette by greater vigor of growth, together with being more upright and having deeper red and more lasting flowers; and in comparison with the Red Imp by a plant which is larger and heavier, with darker, larger, and less double red flowers.

No references cited.